United States Patent [19]
Maurer

[11] Patent Number: 5,633,387
[45] Date of Patent: May 27, 1997

[54] PROCESS FOR PRODUCING 1-(2-CHLOROPHENYL)-5(4H)-TETRAZOLINONE

[75] Inventor: Fritz Maurer, Tochigi, Japan

[73] Assignee: Nihon Bayer Agrochem K.K., Tokyo, Japan

[21] Appl. No.: 631,316

[22] Filed: Apr. 10, 1996

[30] Foreign Application Priority Data

Apr. 17, 1995 [JP] Japan .................................. 7-114049

[51] Int. Cl.⁶ .................................. C07D 257/04
[52] U.S. Cl. .................................. 548/251; 548/250
[58] Field of Search .................................. 548/251, 250

[56] References Cited

U.S. PATENT DOCUMENTS

| | | | |
|---|---|---|---|
| 3,489,763 | 1/1970 | Gates et al. | 260/307 |
| 4,186,131 | 1/1980 | Kreighbaum et al. | 546/210 |
| 4,399,285 | 8/1983 | Förster et al. | 548/251 |

FOREIGN PATENT DOCUMENTS

| | | |
|---|---|---|
| 0029183 | 5/1981 | European Pat. Off. . |
| 0149269 | 7/1985 | European Pat. Off. . |
| 0278542 | 8/1988 | European Pat. Off. . |
| 0638561 | 2/1995 | European Pat. Off. . |
| 0643049 | 3/1995 | European Pat. Off. . |
| 2387969 | 11/1978 | France . |

OTHER PUBLICATIONS

"Comprehensive Heterocyclic Chemistry", A. Katritzk et al., eds., vol. 5, section 4, 13, pp. 792–838, Pergamon Press, New York (1984).
J.Org.Chem. 32(11), 3580–93 (1967).
J.Org.Chem. 45, 5130–36 (1980).
J. Am.Chem.Soc., vol. 81, 3076–79 (1959).
Angew. Chem. Internat. Edit./Vo. 1 (1962) No. 12 pp. 647–651.

*Primary Examiner*—David B. Springer
*Attorney, Agent, or Firm*—Sprung Horn Kramer & Woods

[57] ABSTRACT

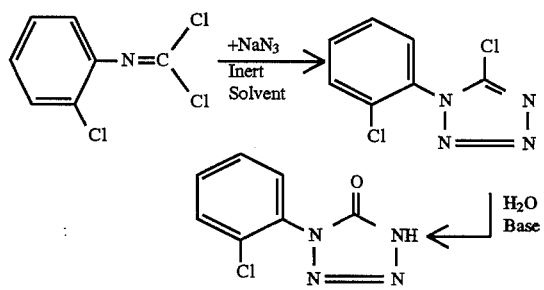

The intermediate is new. The reactions are also new and may be effected separately or as a one-pot process without isolation or purification of the intermediate.

6 Claims, No Drawings

PROCESS FOR PRODUCING 1-(2-CHLOROPHENYL)-5(4H)-TETRAZOLINONE

The present invention relates to a process for producing 1-(2-chlorophenyl)-5(4H)-tetrazolinone, to a novel intermediate therefor and to a process for the preparation thereof.

1-Substituted-5(4H)-tetrazolinones, in general, have been synthesized by processes represented by the following reaction equation A.

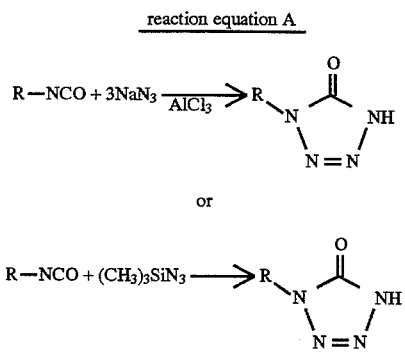

These processes have problems as mentioned below and hence they are not adequately useful for an industrial production process.

(i) A reaction of an anhydrous system is employed, and thus it is difficult to conduct handling and to set up reaction conditions.

(ii) In the above reaction (1) using aluminum chloride, while 1 mole of sodium azide only is reacted with 1 mole of isocyanate, the remaining 2 moles of sodium azide are decomposed and wasted. Furthermore, sodium azide is expensive. Therefore, it is uneconomical.

(iii) Aluminum chloride used as a catalyst in the above reaction (1) has difficulties in waste water treatment.

(iv) Azidotrimethylsilane used in the above reaction (2) is more expensive than sodium azide. Further, in some cases, the yield is low even when the reaction time is extended.

It has now been found that 1-(2-chlorophenyl)-5(4H)-tetrazolinone can be obtained when 1-(2-chlorophenyl)-5-chlorotetrazole is hydrolyzed, in the presence of a base, and in the presence of an inert solvent.

In the process of the invention, the handling and the setting up of reaction conditions are simpler and the solvent and the base used are more inexpensive as compared with the above-mentioned known production processes. Furthermore, according to the invention, since the by-products are only alkali chlorides alone and the desired compound can be synthesized in high yield and purity, various advantages are realized, e.g. it is easy to purify after reaction, and the like. Therefore, the process of the invention is extremely suitable for producing 1-(-2-chlorophenyl)-5(4H)-tetrazolinone on an industrial scale.

In the process of the invention, it is possible to obtain 1-(2-chlorophenyl)-5(4H)-tetrazolinone in a high yield at high temperature and under strongly alkaline conditions, even though this compound is susceptible to decomposition under such high temperature and high alkaline conditions.

The process of the invention is illustrated by the following equation, for example, sodium hydroxide is used as the base.

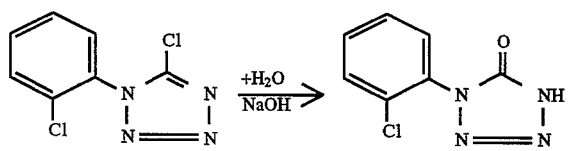

The process of the invention can be carried out in any solvent which is inert to a strong alkali. Examples of the useful solvents include, for example, the following solvents: water; ethers (e.g. ethyl ether, methyl ethyl ether, methyl t-butyl ether, isopropyl ether, butyl ether, dioxane, dimethoxyethane (DME), tetrahydrofuran (THF), diethylene glycol dimethyl ether (DGM), etc.); ketones (e.g. acetone, methyl ethyl ketone (MEK), methyl isopropyl ketone, methyl isobutyl ketone (MIBK), etc.); aliphatic, alicyclic or aromatic hydrocarbons (which may optionally be chlorinated) (e.g. pentane, hexane, cyclohexane, petroleum ether, ligroin, benzene, toluene, xylene, chlorobenzene, dichlorobenzene, etc.).

Furthermore, a mixed solvent of two or more of those can also be used.

The process of the invention is carded out in the presence of bases. The bases which are uses therefor include one or more of hydroxides, carbonates and bicarbonates of alkali metals and alkaline earth metals (e.g. sodium hydrogencarbonate, potassium hydrogencarbonate, sodium carbonate, potassium carbonate, lithium hydroxide, sodium hydroxide, potassium hydroxide, calcium hydroxide, barium hydroxide, magnesium hydroxide, etc.) and others.

The process of the invention can be carded out at a temperature within a substantially broad range, but generally it is suitable to conduct it at a temperature within the range of about 50 ° C. to about 160° C., preferably about 80° C. to about 140° C.

Usually, the process of the invention should desirably be conducted under normal pressure but it may optionally be conducted under elevated or reduced pressure.

In the process of the invention, the reaction time is usually about 0.5 minutes to about 60 minutes, preferably about 1 minute to about 10 minutes, under the above-mentioned conditions.

According to the process of the invention, 1-(2-chlorophenyl)-5(4H)-tetrazolinone can be obtained, for example, by hydrolyzing 1-(2-chlorophenyl)-5-chlorotetrazole in the presence of about one to four-fold the molar amount of the base (such as sodium hydroxide) and in the presence of water.

1-(2-Chlorophenyl)-5-chlorotetrazole which is used as a starting material in the above-mentioned process of the invention is a novel compound, and thus the invention also extends to 1-(2-chlorophenyl)-5-chlorotetrazole and its preparation. 1-(2-Chlorophenyl)-5-chlorotetrazole can quantitatively be obtained by reacting 2-chlorophenylisocyanide dichloride with sodium azide, in the presence of inert solvents.

The reaction is shown by the following reaction equation C.

reaction equation C

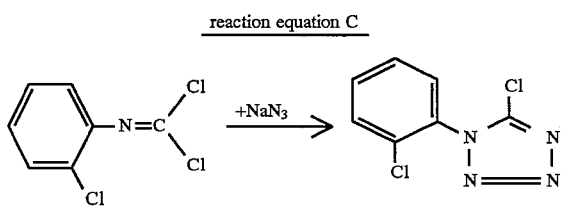

This reaction can be conducted, for example, by a process similar to that described in Journal of Organic Chemistry, Vol. 32, No. 11, pp. 3580–92.

The reaction for producing the 1-(2-chlorophenyl)-5-chlorotetrazole is preferably conducted in inert solvents. Examples of the useful solvents include, for example, the following:

- water; ethers (e.g. ethyl ether, methyl ethyl ether, methyl t-butyl ether, isopropyl ether, butyl ether, dioxane, dimethoxyethane (DE), tetrahydrofuran (THF), diethylene glycol dimethyl ether (DGM), etc.); ketones (e.g. acetone, methyl ethyl ketone (MEK), methyl isopropyl ketone, methyl isobutyl ketone (MIBK), etc.); aliphatic, alicyclic or aromatic hydrocarbons (which may optionally be chlorinated) (e.g. pentane, hexane, cyclohexane, petroleum ether, ligroin, benzene, toluene, xylene, chlorobenzene, dichlorobenzene, etc.); nitriles (e.g. acetonitrile, propionitrile, acrylonitrile, etc.).

Furthermore, a mixed solvent of two or more of those can also be used.

The above reaction can be carried out at a temperature within a substantially broad range, but generally it is suitable to conduct it at a temperature within the range of about 20° C. to about 120° C., preferably about 40° C. to about 100° C.

Usually, the process of the invention should desirably be conducted under normal pressure but it may optionally be conducted under elevated or reduced pressure.

In the above reaction, 1-(2-chlorophenyl)-5-chlorotetrazole can be obtained, for instance, by reacting 1 mole of 2-chlorophenylisocyanide dichloride with about 1 mole to about 1.2 moles of sodium azide in a diluent, for example, a mixed solvent of water and acetone.

2-Chlorophenylisocyanide dichloride used as the starting material in the above reaction is a compound which is known per se, described in Angew. Chem., Vol. 74, page 861, 1962 and the like, and which can be produced by a process described in the literature.

1-(2-Chlorophenyl)-5-chlorotetrazole which is obtainable by the above reaction equation (C) can be isolated, but, according to the invention, in one-pot, without isolation and purification, it can be directly subjected to the abovementioned hydrolysis of reaction equation (B) (one-pot synthetic process).

According to the invention, there is thus further provided a one-pot process for synthesizing 1-(2-chlorophenyl)-5(4H)-tetrazolinone which comprises reacting 2-chlorophenylisocyanide dichloride with sodium azide in inert solvents and then hydrolyzing the resulting 1-(2-chlorophenyl)-5-chlorotetrazole, without isolation or purification, by adding bases and optionally water to the reaction mixture.

This one-pot process has various advantages, e.g. it is easy to conduct and to set up reaction conditions, the desired compound can be synthesized in high yield, the by-products are only alkali chlorides and thus treatment after the reaction can easily be conducted, the used solvent can be reused, and the like. Therefore, it is extremely suitable for producing 1-(-2-chlorophenyl)-5(4H)-tetrazolinone on an industrial scale.

The reaction in each step of the above one-pot synthetic process can be carded out under the above-mentioned reaction conditions.

The formed 1-(2-chlorophenyl)-5(4H)-tetrazolinone can be isolated and purified by a method which is known per se, such as extraction, chromatography, recrystallization, etc.

The following examples illustrate the processes of the invention, but they should not be regarded as limiting the invention in any way.

EXAMPLE 1

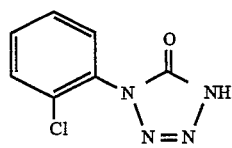

A solution of sodium hydroxide (13 g, about 45% by weight) in water, 1-(2-chloro-phenyl)-5-chlorotetrazole (12.9 g) in water (6.5 ml) were mixed and the mixture was heated to 110° C. The reaction was initiated and the temperature increased to 115° C. After 3 minutes from the initiation of the reaction, the temperature was lowered to room temperature and then water (20 ml) was added. The insoluble matter was extracted with toluene (10 ml) and the aqueous solution was adjusted to a pH of 1. The solid matter was collected by filtration followed by washing with water and drying to obtain a pale tan solid 1-(2-chlorophenyl)-5(4H)-tetrazolinone (11.3 g) (yield: 96%). melting point: 123°–125° C.

EXAMPLE 2

(production of the starting material used in Example 1)

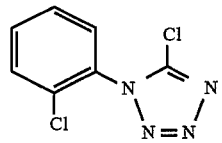

To a solution of sodium azide (3.9 g) in water (20 ml) 2-chlorophenylisocyanide dichloride (12.9 g) dissolved in acetone solution (50 ml) was added with stirring. As the reaction proceeded, the temperature was elevated and reached about 50 ° C. After stirring 15 minutes while maintaining the temperature of 50 ° C., the mixture was heated for 30 minutes under refluxing. Acetone was distilled off under reduced pressure, water (20 ml) was added to the residue, and product collected by filtration under reduced pressure. After washing, this was dried to obtain colorless 1-(2-chlorophenyl)-5-chlorotetrazole (12.9 g) (yield: quantitative). melting point: 101°–103° C.

EXAMPLE 3

(one-pot synthesis)

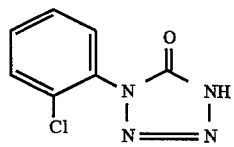

To sodium azide (0.65 g) dissolved in water (3.5 ml) a solution of 2-chlorophenylisocyanide, dichloride (2.09 g) in acetone (8 ml) was added with stirring. The mixture was heated to 50° C. and stirred for 15 minutes while maintaining this temperature. Thereafter, the mixture was heated for further 30 minutes with refluxing. An aqueous sodium hydroxide solution (about 40%, 2.5 g) and water (5 ml) were added thereto and the mixture was heated for 5 hours under stirring. After completing the reaction, the organic solvent was distilled off under reduced pressure and the water layer was washed once with toluene (5 ml). The mixture was adjusted to a pH of 1 with hydrochloric acid and the precipitate was collected by filtration with suction. The precipitate was washed with water followed-by drying to obtain light tan crystals 1-(2-chlorophenyl)-5(4H)-tetrazolinone (yield: 94%). melting point: 122°–124° C.

Reference Example (production of the starting material used in Examples 2 and 3)

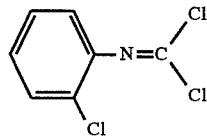

To a mixture of thionyl chloride (150 ml) and sulfuryl chloride (67.5 g) N-(2-chlorophenyl)-formamide (77.5 g) was added at a temperature of 15°–20° C. After stirring the mixture for 3 hours at room temperature, it was heated to 80° C. and stirred for 30 minutes. After completing the reaction, thionyl chloride was distilled off under reduced pressure to obtain 2-chlorophenyl-isocyanide dichloride (yield: 86.7%). boiling point: 104°–106° C./10mmHg (13.3 mbar).

It will be understood that the specification and examples are illustrative but not limitative of the present invention and that other embodiments within the spirit and scope of the invention will suggest themselves to those skilled in the art.

I claim:

1. A process for producing 1-(2-chlorophenyl)-5(4H)-tetrazolinone which comprises hydrolyzing 1-(2-chlorophenyl)-5-chlorotetrazole, in the presence of a base and an inert solvent.

2. The process according to claim 1, wherein the base is at least one member selected from the group consisting of a hydroxide, carbonate and bicarbonate of an alkali metal or alkaline earth metal.

3. The process according to claim 1, wherein the hydrolysis is conducted at a temperature of about 50° C. to about 160° C.

4. The process according to claim 1, wherein 2-chlorophenylisocyanide dichloride is first reacted with sodium azide in the inert solvent, to produce a solution of the 1-(2-chlorophenyl)-5-chlorotetrazole, and then without isolation or purification, to the solution there is added the base and optionally water.

5. The process according to claim 4, wherein the reaction of the 2-chlorophenylisocyanide dichloride with sodium azide is effected at a temperature of about 20° C. to about 120° C., the base comprises at least one member selected from the group consisting of a hydroxide, carbonate and bicarbonate of an alkali metal or alkaline earth metal, and the hydrolysis is effected at a temperature of about 50° C. to about 160° C.

6. 1-(2-Chlorophenyl)-5-chlorotetrazole of the formula:

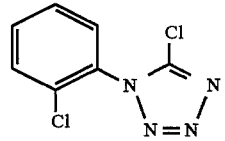

* * * * *